United States Patent [19]
Buirge et al.

[11] Patent Number: 5,693,085
[45] Date of Patent: Dec. 2, 1997

[54] STENT WITH COLLAGEN

[75] Inventors: Andrew W. Buirge, Minnepaolis; Paul J. Buscemi, Long Lake; Paul H. Burmeister, Maple Grove, all of Minn.

[73] Assignee: SciMed Life Systems, Inc., Maple Grove, Minn.

[21] Appl. No.: 429,308

[22] Filed: Apr. 26, 1995

Related U.S. Application Data

[63] Continuation-in-part of Ser. No. 350,223, Dec. 6, 1994, which is a continuation-in-part of Ser. No. 235,300, Apr. 29, 1994.

[51] Int. Cl.⁶ ...................................................... A61F 2/06
[52] U.S. Cl. ........................... 623/1; 623/12; 606/192; 606/194
[58] Field of Search ................... 623/1, 12; 606/192, 606/194, 195

[56] References Cited

U.S. PATENT DOCUMENTS

| | | |
|---|---|---|
| 3,272,204 | 9/1966 | Artandi et al. ........................ 623/1 |
| 3,563,228 | 2/1971 | Seiderman ............................ 128/1 |
| 3,758,396 | 9/1973 | Vieth et al. . |
| 3,892,648 | 7/1975 | Phillips et al. . |
| 4,082,507 | 4/1978 | Sawyer . |
| 4,190,909 | 3/1980 | Ablaza . |
| 4,252,759 | 2/1981 | Yannas et al. . |
| 4,319,363 | 3/1982 | Ketharanathan . |
| 4,378,017 | 3/1983 | Kosgi et al. . |
| 4,503,569 | 3/1985 | Dotter . |
| 4,512,338 | 4/1985 | Balko et al. . |
| 4,591,456 | 5/1986 | Huc et al. . |
| 4,655,771 | 4/1987 | Wallstein . |
| 4,732,152 | 3/1988 | Wallsten et al. . |
| 4,733,665 | 3/1988 | Palmaz . |
| 4,739,762 | 4/1988 | Palmaz . |
| 4,776,337 | 10/1988 | Palmaz . |
| 4,801,299 | 1/1989 | Brendel et al. . |
| 4,835,102 | 5/1989 | Bell et al. . |
| 4,837,379 | 6/1989 | Weinberg . |
| 4,842,575 | 6/1989 | Hoffman, Jr. et al. . |
| 4,848,343 | 7/1989 | Wallsten et al. . |
| 4,902,290 | 2/1990 | Fleckenstein et al. . |
| 4,902,508 | 2/1990 | Badylak et al. . |
| 4,950,178 | 8/1990 | Badylak et al. .................... 623/1 |
| 4,950,227 | 8/1990 | Savin et al. . |
| 4,950,483 | 8/1990 | Ksander et al. . |
| 4,954,126 | 9/1990 | Wallsten . |
| 4,956,178 | 9/1990 | Badylak et al. . |
| 4,986,831 | 1/1991 | King et al. ........................... 623/1 |
| 5,019,090 | 5/1991 | Pinchuk . |
| 5,024,841 | 6/1991 | Chu et al. . |
| 5,026,381 | 6/1991 | Li . |
| 5,037,377 | 8/1991 | Alonso . |
| 5,061,275 | 10/1991 | Wallsten et al. . |
| 5,061,276 | 10/1991 | Tu et al. . |
| 5,100,429 | 3/1992 | Sinofsky et al. . |
| 5,106,949 | 4/1992 | Kemp et al. . |
| 5,108,424 | 4/1992 | Hoffman, Jr. et al. . |

(List continued on next page.)

FOREIGN PATENT DOCUMENTS

| | | |
|---|---|---|
| 0 150 608 | 8/1985 | European Pat. Off. . |
| 0 274 846 B1 | 7/1988 | European Pat. Off. . |
| 0 361 957 A1 | 4/1990 | European Pat. Off. . |
| 0 403 139 A1 | 12/1990 | European Pat. Off. . |

(List continued on next page.)

OTHER PUBLICATIONS

ASAIO Journal, vol. 39, No. 3, pp. M518–M521, Development of a Chronic Endothelialized Transcatheter Implantable Intraaortic Graft, Masaaki Kato, et al.

AJR: 151, Oct. 1988, pp. 673–676, Self–Expanding Graft: An Experimental Study in Dogs, Tetsuya Yoshioka, et al.

(List continued on next page.)

*Primary Examiner*—John G. Weiss
*Assistant Examiner*—Bruce E. Snow
*Attorney, Agent, or Firm*—Vidas, Arrett & Steinkraus, P.A.

[57] ABSTRACT

Collagen applied to a vascular stem for increasing the biocompatability of the stent on implantation find method of treatment.

37 Claims, 6 Drawing Sheets

U.S. PATENT DOCUMENTS

| | | |
|---|---|---|
| 5,110,604 | 5/1992 | Chu et al. . |
| 5,131,907 | 7/1992 | Williams et al. ............................ 600/36 |
| 5,131,908 | 7/1992 | Dardik et al. . |
| 5,147,370 | 9/1992 | McNamara et al. ........................ 623/1 |
| 5,151,105 | 9/1992 | Kwan-Gett . |
| 5,192,311 | 3/1993 | King et al. . |
| 5,195,984 | 3/1993 | Schatz . |
| 5,197,977 | 3/1993 | Hoffman, Jr. et al. . |
| 5,201,764 | 4/1993 | Kelman et al. . |
| 5,234,456 | 8/1993 | Silvestrini . |
| 5,234,457 | 8/1993 | Andersen . |
| 5,256,418 | 10/1993 | Kemp et al. . |
| 5,258,042 | 11/1993 | Mehta . |
| 5,263,983 | 11/1993 | Yoshizato et al. . |
| 5,275,826 | 1/1994 | Badylak et al. . |
| 5,281,422 | 1/1994 | Badylak et al. . |
| 5,282,823 | 2/1994 | Schwartz et al. . |
| 5,304,121 | 4/1994 | Sanatjian ................................. 606/194 |
| 5,316,023 | 5/1994 | Palmaz et al. ............................. 623/1 |
| 5,336,518 | 8/1994 | Narayanan et al. . |
| 5,342,387 | 8/1994 | Summers . |
| 5,360,443 | 11/1994 | Barone et al. ............................. 623/1 |
| 5,376,376 | 12/1994 | Li . |
| 5,383,928 | 1/1995 | Scott et al. . |
| 5,389,106 | 2/1995 | Tower . |
| 5,464,650 | 11/1995 | Berg et al. ............................... 427/2.3 |

FOREIGN PATENT DOCUMENTS

| | | |
|---|---|---|
| 1 418 035 A1 | 3/1991 | European Pat. Off. . |
| 0 493 788 A1 | 7/1992 | European Pat. Off. . |
| 0 621 015 A1 | 10/1994 | European Pat. Off. . |
| 2 187 463 | 9/1987 | United Kingdom . |
| WO 82/01647 | 5/1982 | WIPO . |
| WO 93/06791 | 4/1993 | WIPO . |
| WO 93/15785 | 8/1993 | WIPO . |
| WO 93/20757 | 10/1993 | WIPO . |
| WO 93/21860 | 11/1993 | WIPO . |

OTHER PUBLICATIONS

Radiology, vol. 163, May 1987, 163(2), pp. 357–360, Percutaneous Endovascular Graft: Experimental Evaluation[1], David D. Lawrence, Jr., MD, et al.

Circulation, vol. 77, No. 1, Jan. 1988, pp. 188–199, Implantation of balloon–expandable intravascular grafts by catheterization in pulmonary arteries and systemic veins, Charles E. Mullins, M.D., et al.

Journal of Vascular Surgery, vol. 18, No. 2, Aug. 1993, pp. 299–302, Percutaneous transfemoral insertion of a stented graft to repair a traumatic femoral arteriovenous fistuls, Michael L. Marin, MD, et al.

Journal of Vascular Surgery, vol. 18, No. 6, Dec, 1993, pp. 1056–1059, Transluminal placement of a prosthetic graft–stent device for treatment of a subclavian artery aneurysm, James May, MS, FRACS, FACS, et al.

Journal of Vascular Surgery, vol. 19, No. 4, Apr. 1994, pp. 585–593, The role of circulating cells in the healing of vascular prostheses, Stewart M. Scott, MD, et al.

Restenosis Summit VI, Poster Session Call for Abstracts, Biosynthetic Collagen Coated Endovascular Prostneses; Concept Feasibility, Paul Termin DVM PhD, Rob M. Carr BS, Organogenesis, Canton MA.

STENT WITH COLLAGEN

CROSS-REFERENCE TO RELATED APPLICATION

This application is a Continuation-in-part of application Ser. No. 08/350,223, file Dec. 6, 1994 which application is a Continuation-in-part of application Ser. No. 08/235,300, filed Apr. 29, 1994, the disclosures of which are hereby incorporated by reference.

BACKGROUND OF THE INVENTION

This invention relates to vascular prostheses of improved biocompatability and more specifically to stents in combination with a collagen material. Such a combination provides an endovascular stent which protects the vascular wall and forms a non-thrombogenic cushion for the stent in the vascular lumen.

It also relates to stents in combination with a collagen liner material. Such a combination provides an endoluminal stent which engages the luminal wall and in the case of vascular applications, forms a non-thrombogenic surface as well as providing for the growth of endothelial cells, as well as a reservoir or point of attachment for therapeutic agents in any application.

It also relates to combinations of both of the foregoing arrangements.

Broadly, it relates to stents associated with an outer covering of collagen material and/or a luminal liner of same. It also relates to a method of applying collagen to the interior of a vessel or the like as a liner by using a stent.

Stents are generally tubular in configuration, are open ended, and are radially expandable between a generally unexpanded insertion diameter and an expanded implantation diameter which is greater than the unexpanded insertion diameter. Such intravascular implants are used for maintaining vascular patency in humans and animals.

Stents are typically placed or implanted by a mechanical transluminal procedure. One common procedure for implanting a stent is to first open the region of the vessels with a balloon catheter and then place the stent in a position that bridges the treated portion of the vessel by means of a placement catheter.

Prior art patents refer to the construction and design of stents as well as apparatus for positioning stents within a vessel. In general, for example, such patents disclose a technique for positioning an elongated cylindrical stent at a region of an aneurysm, stenosis or the like. The stent expands as necessary to an implanted configuration after insertion with the aid of a catheter.

Specifically, U.S. Pat. 4,733,665 to Palmaz which issued Mar. 29, 1988, discloses a number of stent configurations for implantation with the aid of a catheter. The catheter includes means for mounting and retaining the stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel. U.S. Pat. No. 4,950,227 to Savin et al., which issued on Aug. 21, 1990 is similar.

Another similar U.S. Pat. No. 5,019,090 discloses a generally cylindrical stent and a technique for implanting it using a deflated balloon catheter to position the stent within a vessel. Once the stent is properly positioned the balloon is inflated to press the stent against the inner wall linings of the vessel. The balloon is then deflated and withdrawn from the vessel, leaving the stent in place.

A patent to Dotter, U.S. Pat. No. 4,503,569 which issued Mar. 12, 1985 discloses a spring stent which expands to an implanted configuration with a change in temperature. The spring stent is implanted in a coiled orientation and heated to cause the spring to expand due to the characteristics of the shape memory alloy from which the stent is made. Similarly, U.S. Pat. No. 4,512,338 to Balko et at., which issued Apr. 23, 1985, discloses a shape memory alloy stent and method for its delivery and use other kinds of self-expanding stents are known in the art.

Figure 1:
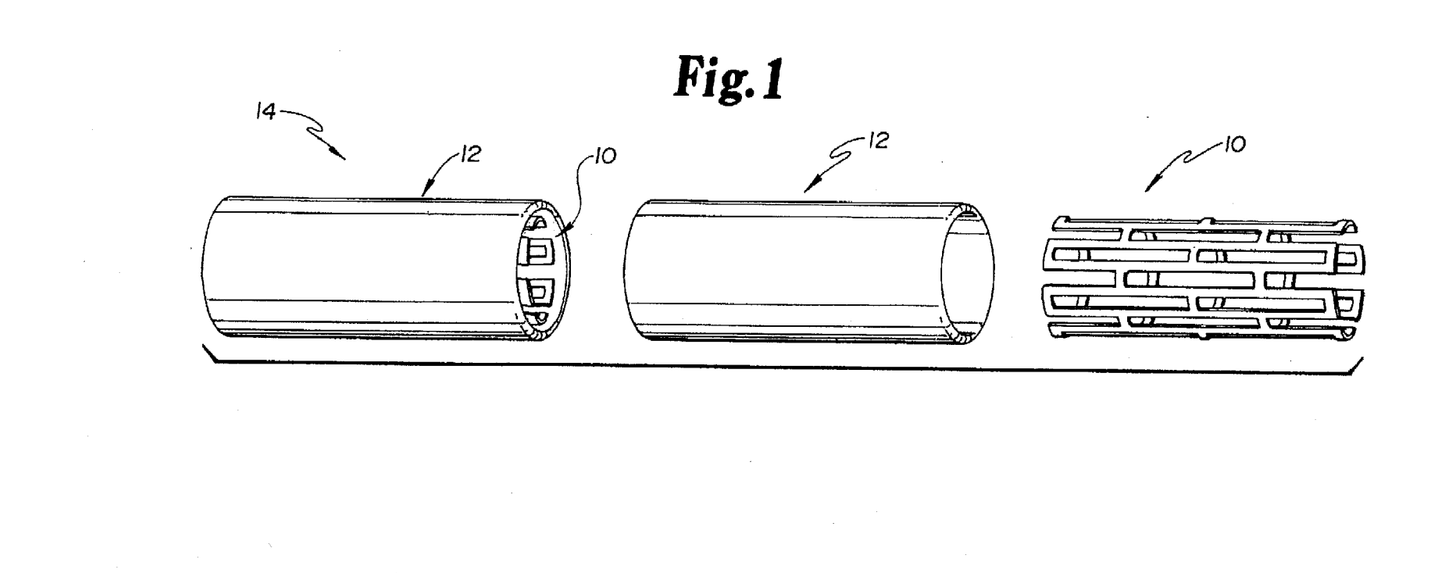
FIG. 1 shows a stent and covering sleeve combination being formed according to the invention.
Figure 6:
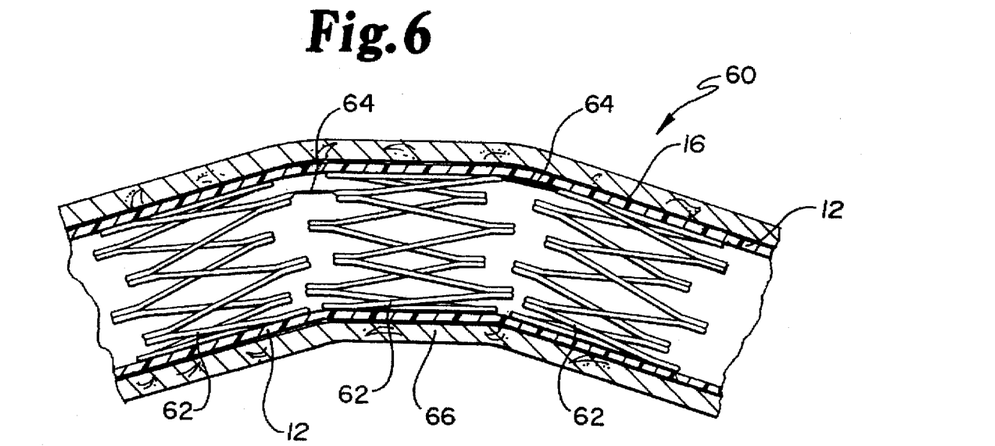

The delivery and expansion of the stent of the invention is the same as that already known in the art and practiced with the stent of FIGS. 1 and 6. U.S. Pat. No. 5,195,984 to Schatz, issued Mar. 23, 1993, describes a typical balloon expansion procedure for an expandable stent. This patent is incorporated in its entirety herein by reference. That patent describes a catheter having an expandable inflatable portion associated therewith. In a conventional manner, the catheter and stent are delivered to a desired location within a body passageway at which it is desired to expand the stent for implantation. Fluoroscopy, and or other conventional techniques may be utilized to insure that the catheter and graft are delivered to the desired location. The stent is then controllably expanded and deformed by controllably expanding the expandable inflatable portion of catheter, typically a balloon. As a result the stent is deformed radially outwardly into contact with the walls of the body passageway. In this regard, the expandable inflatable portion of the catheter may be a convention angioplasty balloon as is already known in the art. After the desired expansion and deformation of the stent has been accomplished, the angioplasty balloon may be deflated and the catheter removed in a conventional manner from the passageway.

Also, this invention is useful in self-expanding stents such as those disclosed in U.S. Pat. Nos. 4,732,152 and 4,848,343, both of which are incorporated herein by reference.

All of the above-identified patents are incorporated herein by reference.

SUMMARY OF THE INVENTION

In one preferred form a metal or other stent is delivered for vascular implantation with a covering sleeve of collagen material. If the stent is of the variable diameter type, the sleeve may be stretched into place or otherwise positioned between the stent and the vascular wall when the stent is seated or deployed. A drug or other agent such as heparin or the like may be included in the collagen for release after stent deployment.

In another preferred form a metal or other stent is delivered for vascular implantation with a luminal liner of collagen material. A drug or other agent such as heparin or the like may be included in the collagen as a surface treatment or for release after stent deployment.

In yet another preferred form, a stent is provided with both an inner collagen liner and outer collagen coating.

DETAILED DESCRIPTION OF THE PREFERRED EMBODIMENT

Referring now to FIG. 1, a tubular metal stent generally indicated at 10 is shown being combined with a covering sleeve of collagen material generally indicated at 12 to provide the combination stent/sleeve generally indicated at 14 for the purpose of vascular implantation.

Stent 10 is of the type, typically of a metal such as for example stainless steel, nitinol, superelastic alloys and other metals or a suitable polymeric plastic and may be of a fixed diameter or of a variable diameter, the latter being more preferred and well known in the art. The variable diameter type are usually either balloon expandable or self-expanding, both of which are also known in the art. Examples of the former type are shown in U.S. Pat. No. 4,733,665, U.S. Pat. No. 4,739,762 and U.S. Pat. No. 4,776,337, all of which are incorporated herein by reference. The latter type is preferred for the purposes of this invention at present, i.e., self-expanding, particularly those made of Nitinol an example of which is discussed in the U.S. Pat. Nos. 4,503,569 and 4,512,338, also incorporated herein by reference. Also, for example, useful stents are shown in co-pending application Ser. No. 08/246,320 filed May 19, 1994 entitled "Improved Tissue Supporting Devices". The content of this application is incorporated herein by reference.

In any event, generally a stent provides a supporting framework structure which may take many forms. Typically stents are open or perforate and may be comprised of a network of struts or wire-like structure. Stent 10 is comprised of struts.

Figure 2:
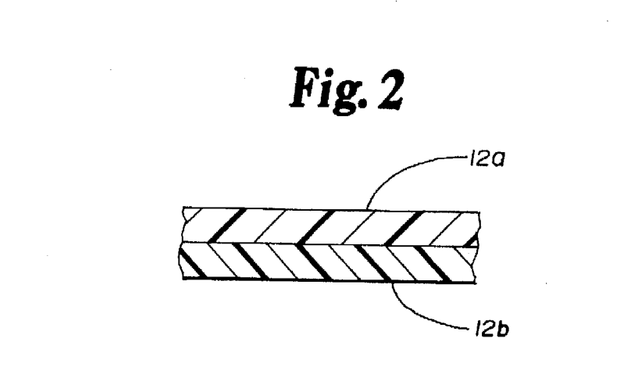
FIG. 2 is a fragmentary showing of collagen with a fabric support.

Collagen sleeve 12 shown in FIG. 1 may be comprised of collagen per se or it 12a may be carried on a support 12b as shown in FIG. 2, support 12b being of DACRON® fabric or the like as is known and disclosed for example in U.S. Pat. Nos. 5,256,418, 5,201,764 and 5,197,977, the entire content of which are all incorporated herein by reference, particularly those portions which relate to the formation of collagen tubes. The Support 12b may be a fabric, woven or braided, and may also be of polyester, polyethylene, polyurethane or PTFE. The term "collagen material" is used herein to refer to both supported and unsupported collagen for the sleeve element of this invention.

The preferred collagen at present appears, for the purposes of this invention, to be that composed of bovine or porcine Type I or Type IV collagen and combinations thereof in bilayer sheet like form. The collagen may also be made of Type III or combinations of any of the various types. U.S. Pat. Nos. 4,837,379; 4,902,508; 4,950,483; 4,956,178; 5,106,949; 5,110,064; 5,256,418; 5,275,826; 5,281,422 and 5,024,841 relate to collagen compositions and production useful in this invention and are incorporated herein by reference. Collagen can be extracted from various structural tissues as is known in the art and reformed into sheets or tubes and dried onto a stent. Generally, the thickness of these sheets or tubes will range from about 5 to 200 microns. One preferred collagen at present is that disclosed in U.S. Pat. No. 4,902,508 coated as described in U.S. Pat. No. 5,275,826 to provide bilayer SIS as described further hereinbelow. Another preferred collagen is that described as a "collagen construct" in U.S. Pat. No. 5,256,418, particularly in which the permeable substrate is also collagen.

Cells of the blood vessel wall synthesize and secrete several kinds of macromolecules forming extracellular matrix. The components of this matrix comprise several large proteins that may be synthetically constructed to form films, tubes or multilayer sheets or other constructs. Among these biological components are collagens of several types, elastin, glycosaminoglycans (GAGS), fibronectin and laminin. Collagens are three chain glycoproteins with molecular weights of about 300,000. Elastin is an insoluble nonpolar amine acid rich crosslinked protein. The GAGs are linear chain polysaccharides with various negative charges with various molecular weights ranging from thousands to millions. Included in the GAGs are heparin and heparin sulfate, dermatin sulfate and chondroitin sulfate. Fibronectin is a 440,000 MW 2-chain adhesive glycoprotein that acts as a substrate for many cell types and in cell-cell interactions. Laminin is a 2 chain glycoprotein of MW about 850,000 and acts as a basement membrane structure for cellular-molecular interactions. Each of these macromolecules may be combined in a multitude of combinations to form composites. These are all natural materials that serve specific functions and are exposed to blood under normal repair conditions. It is therefore expected that, if a covering sleeve for a stent were made of these macromolecules and used in the course of intervention, repair of a blood vessel would proceed more naturally than if a similar device were constructed of synthetic polymers such as polyethylene, polyteraphthalate or polyurethanes. Such materials are also referred to herein generally as "collagen". The term "collagen" herein thus refers to not only the specific class of macromolecules known as collagen but those natural materials that normally or naturally form membranes with collagen such as laminin, keratin, glycosaminoglycans, proteoglycans, pure carbohydrates, fibrin, fibronectin, hyaluronic acid or the like, and other natural materials that come into contact with collagen that can be made into film, including albumin, globulins, and other blood borne proteins. Tubular films made from any combination of the above materials will provide substantially the same purpose as that of pure collagen.

The interaction of blood with the differing membrane components described above determines subsequent reactions in the repair of blood vasculature. The initial thrombus formation adhesion and activation of platelets and the initial events related to intimal hyperplasia such as damage to the internal elastic lamina are among those events. These events are natural components of the repair process. Normally these events do not hamper the flow conditions of blood except in the cases of severe trauma. Microthrombi constantly form and disperse on blood vessel surfaces so it would be advantageous to form stem or graft coverings of materials that are accustomed to having thrombus form so that subsequent lysis reactions of those thrombi can proceed in a natural and unobtrusive manner. A sleeve or liner made of these macromolecular components forming a protective layer will prove advantageous when used with stents. Metal or polymeric stents which will provide mechanical stability to the arterial wall to hold up dissected tissue may also be used to hold a sleeve comprised of collagen.

Nevertheless, because anything not formed in the body as a natural component may elicit extreme and unexpected responses as blood vessel closure due to thrombus formation or spasm and because damage to blood vessels by the act of insertion itself of a device may be extreme and unduly injurious to the blood vessel surface, it is prudent to protect against such events. The materials described above are capable of being manipulated to become hydrophilic or hydrophobic with thicknesses ranging from about 5 to several hundred microns. They can be made water soluble, insoluble and with various porosities. They can also be constructed to have regions of various hydrophilicity and porosity. Porosity control is well known.

As such, stent sleeves or liners constructed of these materials can be used for reservoirs for pharmaceutical agents and the like. Hydrophilic drugs such as heparin or hirudin to protect against coagulation or hydrophobic drugs such as prostaglandins or aspirin and vitamin E may be used to protect against platelet activation. Vitamin E and other anti oxidants such as sodium ascorbate, phendies, carbazoles, and tocotrienols may be used to protect against oxidation. Most preferably, the collagen material will include a quantity of drug material such as heparin which may be incorporated into the collagen in known manner for release after placement of the stent. Generally, the drug materials may include the known antithrombic agents, antibacterial and/or antimicrobial agents, antifungal agents and the like.

During the formation process of the sleeve or sheet, various components may be added to the solution prior to drying or may be added separately after formation of the device. Heparin may be directly added to the forming solution as may be aspirin. Benzalkonium heparin, a modified form of heparin which makes it more hydrophobic may be used to coat the formed device or film from a solution of alcohol. Prostaglandins PGI2 or PGE2 may be added from a solution of propanol or propanol/methylene chloride onto a collagen sleeve formed from an aqueous base. Vitamin E may be added from even less polar solutions as chloroform. RGD peptide, thrombomodulin, TPA (Tissue Plasminogen Activator) and Urokinase are examples of bioactive proteins which may be added. Gene therapy agents such as antiplatelet and antibody fragments, for example GB2B3A may be included. Other agents could be similarly added. The term "agents" is used herein to include all such additives.

Vitamin E is a known antioxidant. It is used in polymers and as a drug. It could also be used in biodegradable stents for multiple purposes. In those polymeric type stents that require some form of energy as heat or light to be delivered it could serve to protect the polymers therein against unwanted oxidation caused by the energy source. Also, because tissue damage is caused by oxidation originating from cellular components as macrophages and neutrophils, Vitamin E could serve to protect the tissue as it leached from implanted devices. It could also serve to protect the polymer during extrusion or heat forming as pressing films. It could also serve to plasticize the material in place of using other non FDA approved materials. It is therefore contemplated that Vitamin E may also be used in combination with the stent or collagen material or the like in this invention for several purposes.

A primary result of the use of a collagen sleeve made of natural components is that cellular regrowth of endothelium will take place onto a natural substrate that is essentially undamaged and uniform and protects against tissue flaps and exposure of necrotic or arthrosclerotic tissue to blood. In this regard, the sleeve provides biological protection.

Metal stents are known to sometimes physically damage tissue upon expansion. A sleeve made of a biological material is naturally soft by comparison to the metals or polymers used to construct stents. A sleeve comprised of collagen may be made sufficiently thick and durable so that it will prevent or at a minimum reduce any damage caused by the struts or other elements of any of the metal stents to the remaining healthy endothelium and the internal elastic lamina. The porosity of the sleeve may permit diffusion of essential fluid components from the blood to the surviving tissue below. In this regard, the benefit of the biological tissue protection by the sleeve and the physical protection provided are additive.

Both the biological and physical advantages as described herein can not be provided by synthetic sleeves as Dacron or PTFE.

In the case of a fixed diameter stent, the sleeve may be fitted to the stent rather closely for ease of vascular placement. However, in the case of variable diameter stents, the sleeve being somewhat elastic will fit the constricted stent and stretch with it upon deployment or it may be relatively loose fitting to accommodate the expanded stent upon deployment without any additional stress. Alternatively and most preferably, the stent may be expanded temporarily and the collagen placed thereon. The collagen may then be hydrated and the stent contracted to its unexpanded configuration. Then the collagen is dehydrated and it fits tightly to the stent.

A sleeve or a liner may be made to be more elastic by altering the crosslink density of the collagen. This can be accomplished in a variety of ways. Collagen sleeves may be prepared to have a very low crosslink density. The crosslink density may be increased in a variety of ways, dehydration, radiation exposure or heating are some examples of ways. Chemical agents which react with the collagen, such as short chain dialdehydes or formaldehyde may be employed to crosslink the collagen. The avoidance of the aforementioned processes can assure a non-crosslinked structure and result in somewhat elastic material. Crosslinking with the appropriate reagents can also enhance the elasticity of the collagen sleeve. Such reagents are the long chain difunctional molecules C12 and higher such as polyether or aliphatic dialdehydes, activated diesters such as N-hydroxy succinimide esters and diacid chlorides. These active esters will react with amines present on the collagen chains thus bridging them by a flexible link which allows expansion without failure and tearing. Also, with amine functionality protected as an amide, the interchain, irreversible amide formation, which results from dehydration, is prevented.

Figure 3:
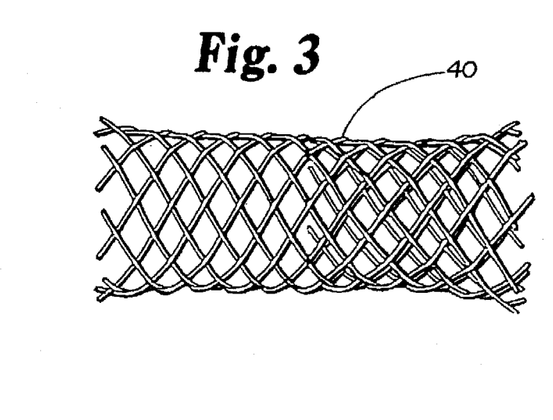
FIG. 3 shows an example of another self-expanding stent configuration useful in the invention.
Figure 4:
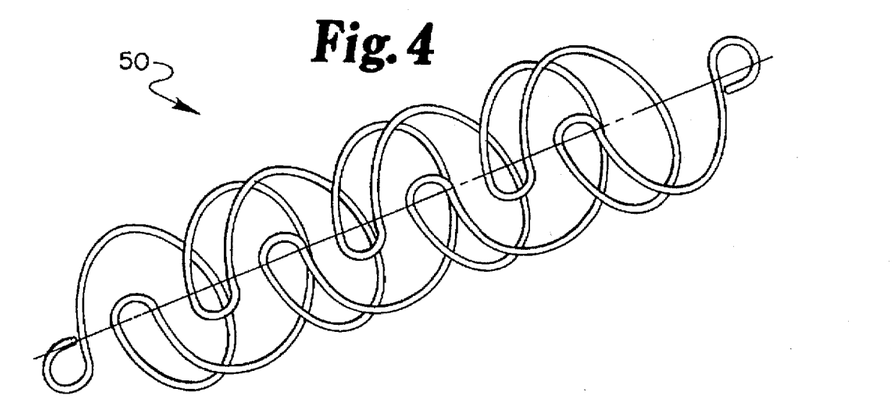
FIG. 4 shows another stent configuration useful in the invention.

A variety of stent types may be used in the invention. Some examples are shown in FIGS. 3–6. In FIG. 3 there is shown a braided self-expanding stent generally designated 40. As is clear from the Figure, stent 40 has a cylindrical configuration. The stent may be manufactured in a braiding machine, wherein the stainless steel monofilaments consist of a plurality of wires, each having a thickness of, for example, 0.08 min. FIG. 4 shows yet another stent configuration 50 which may be used in this invention. Other examples of this type of stent are disclosed in U.S. Pat. No. 4,655,771; U.S. Pat. No. 4,732,152; U.S. Pat. No. 4,954,126 and U.S. Pat. No. 5,061,275; all of which are incorporated herein by reference.

Figure 5:
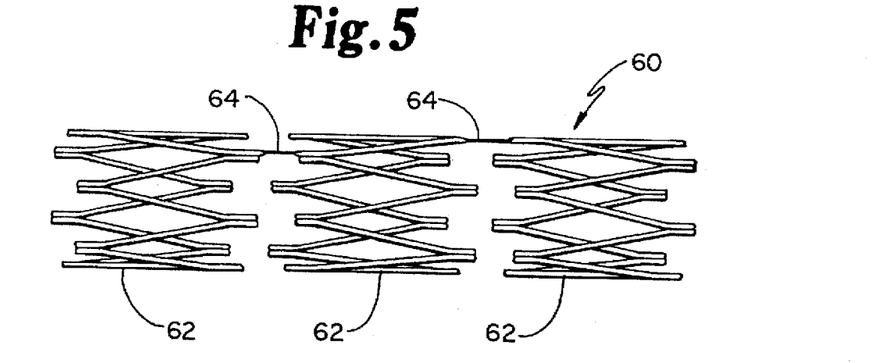
FIGS. 5 and 6 show a flexible stent configuration which may incorporate a covering sleeve according to the invention.

Referring now to FIGS. 5 and 6 an articulated stent 60 is shown with three stent segments 62 and two interconnecting hinge elements 64. Stent segments 62 are each made of individual wire elements welded together. Hinges 64 may be made of biocompatible spring material and may be of a smaller diameter than those used in forming stent segments 62. Hinges 64 are welded at each end to stent segments 62 using either laser or resistance welding techniques. Hinges 64 are preferably both attached to the same side of stent segments 62. Stent 60, shown in FIG. 5, may be installed in an artery 66 with a sleeve 12 as shown in FIG. 6 and may be bent as shown.

Other stent configurations and materials will be apparent to those familiar with this art.

Collagen sleeves may be made to cover both sides of the stent, inside and out so that its surfaces are entirely encompassed by collagen.

Figure 7:
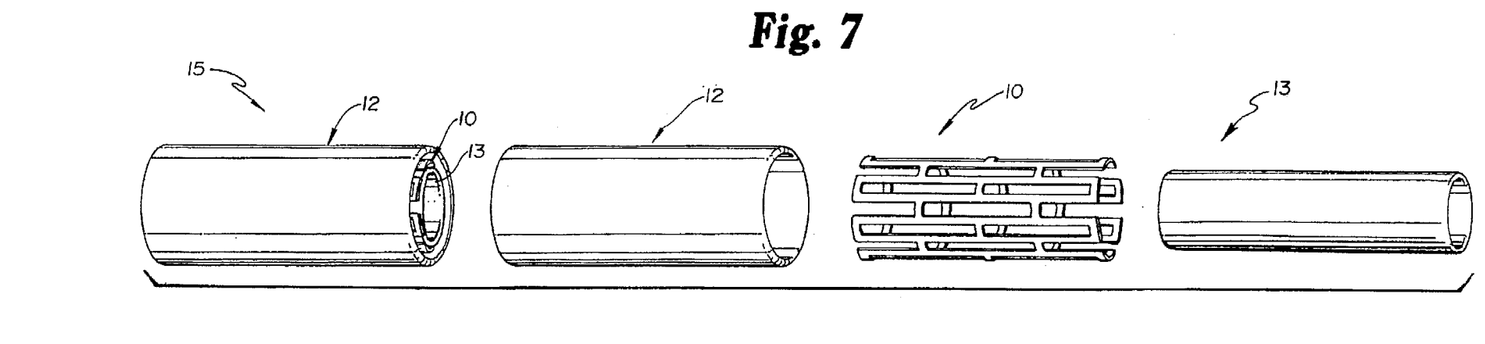
FIG. 7 is similar to FIG. 1, showing a combination being formed including an internal liner and an external sleeve for a stent, according to the invention.

An example of one such embodiment is shown in FIG. 7 which comprises a tubular stent generally indicated at 10 combined with an inner sleeve 13 of collagen material and an outer sleeve 12 of collagen material which provide in combination a stent/sleeve generally indicated at 15 for the purpose of vascular implantation. In some cases, it is preferred that the collagen sleeve 13 be joined to the interior surface of the stent by a suitable means such as collagen gel which acts as an adhesive, particularly when the stent is of the variable diameter type. Such gels are known in the art.

EXAMPLE

Method for the preparation of the sleeve stem of FIG. 7.
1. SIS sheet is stretched about 50% while allowed to air dry.
2. Dry SIS sheet is wrapped onto an inflated, standard angioplasty balloon, moistening along the seam to ensure proper adhesion.
3. A tubular stent is then placed over the SIS.
4. A second sheet of SIS is wrapped over the exterior of the stem. This sheet may be wetted to facilitate handling. The SIS which resides inside the stent may be wetted with a small amount of distilled water immediately preceding this wrapping procedure also.
5. Open cell foam sheeting is then wrapped onto the outer second layer of collagen, followed by a wrap of dialysis tubing. This radial pressure insures continuous contact and adhesion between the collagen layers.
6. The entire construction is then immersed in water momentarily to wet the collagen.
7. The entire combination is then heated to about 40°–70° C. for about 0.5–3 hours, then cooled to room temperature. The purpose of this heat treatment is to bond the collagen layers together. It may optionally be accomplished by use of a chemical cross-linking agent.
8. The resultant device is liberated from the balloon after the dialysis tubing and foam are removed. Any excess collagen material is then trimmed from the ends of the covered stent.

Figure 8:
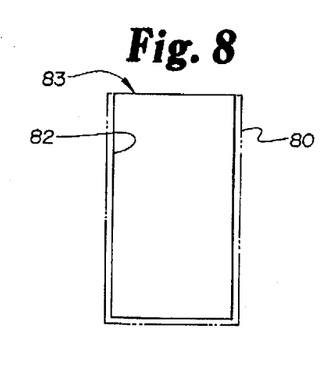
FIG. 8 is a showing of an alternate mode of manufacture of the invention by molding the collagen to the stent.

A cast or molded version is shown being manufactured in FIG. 8 which includes a cylindrical mold 80 into which a cylindrical stent 82 is placed on end. Preferably, mold 80 will be porous, such as a porous ceramic, so as to allow water to be drawn through the mold to facilitate set-up of the poured collagen. A collagen gel solution 83 is then poured into mold 80 around stent 82 and inside of stent 82 and allowed to set-up. Upon set-up, the stent embedded in collagen is removed from the mold and a longitudinal hole may be formed through the collagen inside the stent to provide a longitudinal opening therethrough. Otherwise, a mandrel or mold insert may be used for this purpose as well.

In other embodiments, the collagen material may be coated onto the stent surfaces as desired by spraying or dip coating or an electrophoretic technique or the like. The electrophoretic technique is a preferred coating technique and may be accomplished, for example, in a solution of acetic acid, acetone, water and collagen with a metal stent as the cathode, at a potential of about three volts. This process bears some resemblance to modern electroplating, where positively charged metal ions are reduced to their corresponding metal at the negatively charged cathode. In the case of collagen, the biomolecule is dissolved or suspended in an acidic solution. The acid imparts a positive charge to the protein, collagen, and allows it to travel in an electrical field. By attaching a metal object to the negative electrode of a power source, and then immersing both the positive and negative electrodes in the acidic collagen solution, a layer of collagen will form on the negatively charged surface. The result is a coated stent of the type shown in FIGS. 19 and 20 which will preferably include openings in the coating coincident with the openings in the stent.

EXAMPLE Collagen Coated Stent (Type IV) Via Electrodeposition

A. A solution of Sigma type IV human collagen (50 mg) was placed in a polypropylene tube with 3 ml water, 1 ml of acetic acid and 2 ml of acetone. This mixture was homogenized to a viscous solution via high shear mixing for ca. 3 minutes. The solution was diluted with water, then filtered through a cotton plug. The solution was allowed to stand for 1 hour to eliminate air bubbles.

B. A cylindrical container was fashioned out of polypropylene and charged with 1 ml of the above prepared solution A. To this container was added a nitinol substrate attached to the negative lead of a variable voltage power supply which was set at 3 volts. The positive electrode was furnished with a 0.010 inch diameter wire which was placed ca. 4 mm from the substrate. The power supply was turned on and gas evolution was immediately evident on the surfaces of each electrode. This was maintained for several minutes, then the electrodes were removed from the collagen solution. An even gelatinous mass was evident on the substrate, which contained several bubbles. Upon standing for 1 to 2 minutes, the bubbles were gone, and the electrodes were once again placed in the bath. After three additional minutes of treatment, the substrate was withdrawn from the bath and allowed to dry. The coating appeared to be continuous via visual inspection.

Another coating technique is shown in U.S. Pat. No. 5,275,826 which is incorporated herein by reference.

Figure 9:
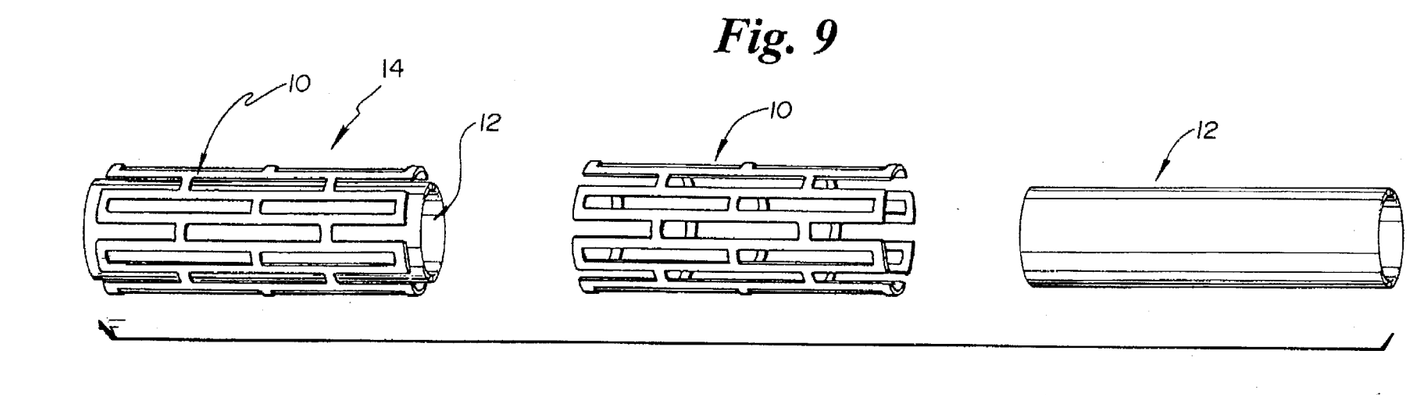
FIG. 9 shows a stent and an internal liner sleeve combination being formed according to the invention.

Referring now to FIG. 9, a tubular metal stent generally indicated at 10 carries within it a cylindrical liner or inner sleeve of collagen material generally indicated at 12 to provide a combination stent/liner generally indicated at 14 for the purpose of vascular implantation.

Stent 10, as already described hereinabove, is of any type, typically a metal such as for example stainless steel, nitinol, superelastic alloys and other metals or a suitable polymer or any other suitable material and may be of a fixed diameter or of a variable diameter, the latter being more preferred and well known in the art. The content of this application is incorporated herein by reference.

Figure 10:
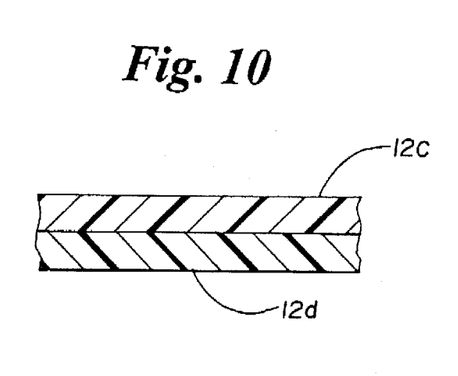
FIGS. 10 shows a bilayer collagen material in schematic and fragmentary form.

Collagen liner 12 as described hereinbefore, may be of collagen per se or it may be applied directly to the stent or it may be carried as 12c on a support 12d as shown in FIG. 10 for application to a stent.

When the collagen liner is comprised of two different materials which are joined together as shown in FIG. 10, it may be referred to as a bilayer structure. When placed in a stem, layer 12c is placed luminally with layer 12d contacting the inner surface of the stent. Layer 12d, which may be in contact with the vessel wall through openings in the stent in such an arrangement, is preferably strong and enables the inner luminal layer 12c itself to have the structural integrity necessary to ensure ease of loading, delivery and deployment. Layer 12c may for example be comprised of a collagenous material in the range of 5 to 200 microns thick. Such a biologically derived material may be harvested from a donor source, cleaned of unwanted tissues and formed into the tube by wrapping it around a mandrel and bonding the material to itself. Synthetic materials may be used to comprise the support of layer 12d of the liner, however, vascular graft materials such as PTFE, woven dacron, polyurethane and the like may also be used. Resorbable polymers (PLLA, PGA, PDLLA, PHB, polyanhydrides) are another choice for the support layer 12d of the liner 12. These materials may be formed into a tube by extrusion, solvent casting, injection molding, etc. or spinning into fibers and weaving into a tubular structure. A tube of one of the aforementioned polymers may also be constructed by a non-woven fiber technique.

The innermost or luminal side, i.e., layer 12c of the liner serves a different function than the support layer 12d. The luminal surface or layer 12c must be a substrate for the growth of endothelial cells, as well as a reservoir for therapeutic agents. Preferred material is fibular Type I collagen and/or porcine Type IV collagen in the range of 5–200 microns thick, although fibrin may also be used for this purpose. Highly hydrated materials, such as cross linked hydrogels meet the drug holding requirement for the luminal portion of the liner, examples of which are polyethers, polyalcohols, polypyrollidones, polypeptides, polyacids and the like. The layer 12 may also be a mixture of the above materials with a drug binding, ionic or covalent, molecule. One such molecule would be protamine, which effectively ionically binds heparin. These polymers can also be treated with growth factors, such as RGD peptides to promote endothelialization. The preferred method of drug incorporation would involve the preparation of a solution of the therapeutic agent and allowing the dehydrated luminal side of the sleeve to swell with the solution. Upon evaporation of the carrier solvent, the drug would be made to reside in the matrix which comprises the inner layer of the liner, i.e., layer 12c. The device may act as a sponge to soak-up a drug in solution and to elute it from the stent upon implantation.

The term "collagen" or "collagen material" should also be understood to include the material referred to as Small Intestine Submucosa (SIS) which has particular use in this invention, alone and in combination with other collagen material such as Type I. SIS is comprised of a bilayer structure in which one layer is predominantly (stratum compactum) Type IV and the second layer is a mixture of Type I (muscularis mucosa) and Type III material. It is described in detail in U.S. Pat. Nos. 4,902,508; 4,956,178 and 5,281,422, all of which are incorporated herein by reference. The luminal side of the SIS as used in preferred embodiments of this invention are predominantly a Type IV collagen material.

As with other collagen material, SIS may be used herein with or without a support layer such as a layer 12d as shown in FIG. 10. It may also be used as the support layer 12c in combination with a layer 12d of Type I collagen as shown in FIG. 10. SIS functions well without a support layer because it is itself a multi-layer structure.

Figure 11:
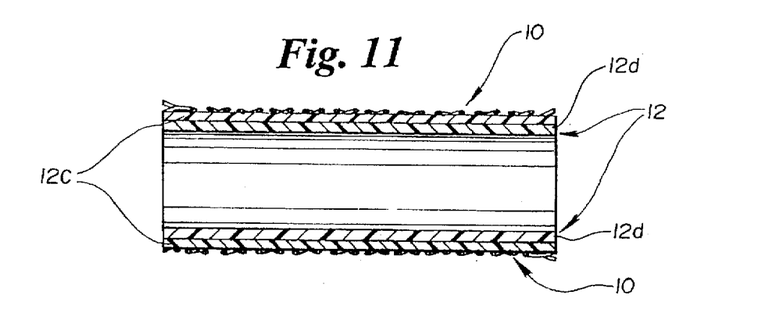
FIGS. 11, 12, and 13 are schematic longitudinal cross-sectional views of a stent carrying inner and outer layers of collagen material.

In yet another embodiment, an SIS layer may be combined with a Type I layer to provide a one-way flow structure with reservoir arrangement as shown schematically in FIG. 11. In this arrangement, a cylindrical wire mesh stent 10 carries a tubular bilayer liner generally indicated at 12 comprised of two layers 12c and 12d. Layer 12c contacts the inner surface of stent 10 and is a Type I collagen material and may carry a drug or the like, acting as a reservoir. Luminal layer 12d is SIS material and inherently functions to allow flow of drug from layer 12c into the luminal interior of the stent through the luminal layer 12d of stent 10 but does not permit appreciable fluid flow into layer 12c from the interior of the stent.

Figure 12:
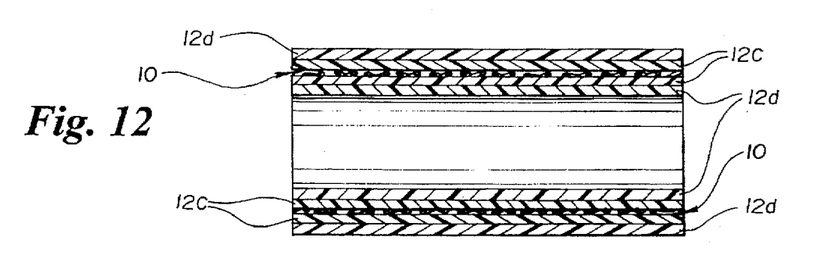
Figure 13:
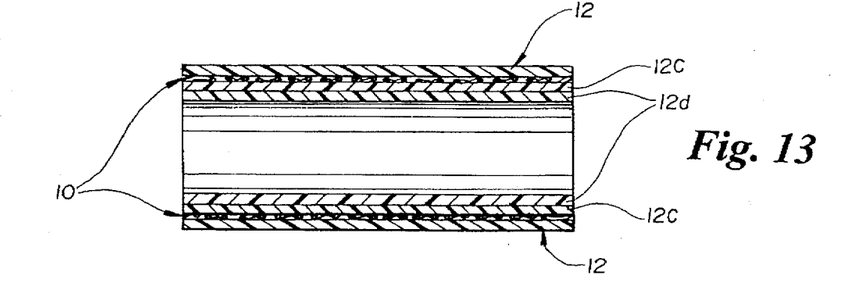

Variations of this FIG. 11 arrangement are shown in FIGS. 12 and 13. In FIG. 12, stent 10 carries an inner or luminal liner made up of layers 12c and 12d as described for FIG. 11 and an outer layer of the same combination to allow predominantly one-way flow of drug to the luminal interior of the stent and to the surface against which the stent rests when implanted.

In FIG. 13, stent 10 carries an exterior layer 12 of unsupported SIS material and an inner liner comprised of layers 12c and 12d as in FIGS. 11 and 12. Layer 12c is Type I material acting as a drug reservoir as previously shown in FIGS. 11 and 12. Layer 12d is of SIS acting as the one-way flow-through for drugs and the like from layer 12c, as before.

As pointed out hereinabove, cells of the blood vessel wall synthesize and secrete several kinds of macromolecules forming extracellular matrix. Each of these macromolecules may be combined in a multitude of combinations to form composites. Such materials as already pointed out, are referred to herein generally as "collagen".

A primary result of the use of a collagen liner made of natural components is that cellular regrowth of endothelium will take place onto a natural surface that is essentially undamaged and uniform. In this regard, the liner provides biological protection.

The liner may be tightly fitted to the stent in much the same way as described hereinabove with reference to the outer sleeve arrangement.

Figure 14:
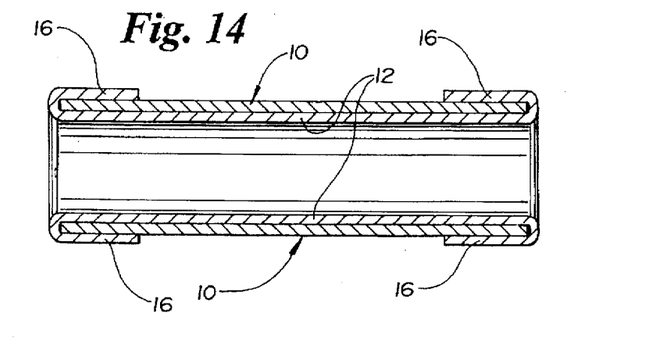
FIG. 14 is a showing of an alternate stent/liner arrangement.

The liner may be attached to the stent in a wide variety of ways. The basic goal of attachment in the preferred form is to provide a stent device in which the supporting stent framework is substantially, if not completely, isolated from the blood flow by the liner. This can be achieved by placing liner 12 in the inside dimension of the stent 10 and cuffing the ends of the liner over the ends of the stent as shown at 16 in FIG. 14. This is an especially preferred arrangement. Cuffs 16 may either be under or over the outer sleeve. Cuffs 16 may be sutured to the stent, sutured from one cuff to the other, or otherwise bonded to the stent or to the liner itself. The collagen material may be welded, by the application of localized heat and pressure, or the application of a concentrated solution of collagen material which acts like glue.

The liner may also be attached to the stent by the use of pledgets (not shown). The pledget (or small swatch of material) can be placed on the outside of the stent. The liner, which resides on the luminal or inner surface of the stent, may be bonded to the pledget in a variety of ways. Among these are suturing, gluing and heat welding. In the case of a combination of liner with outer sleeve, these means of attachment may be used as well.

The liner may be placed in the stent via several methods. The stent may be made porous or perforated, thus allowing the liner material to act as a forming mandrel for a collagen sleeve. The collagen may also be precipitated onto the stent. This method would require the stent to be heated in a solution of collagen. The collagen forms a matrix on the surface of the stent, then when properly annealed, the collagen assumes a fibular, well organized structure conducive for the attachment and growth of cells.

Figure 15:
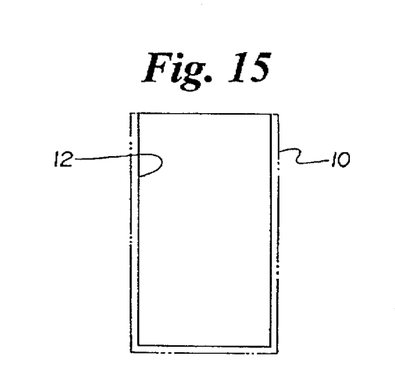
FIG. 15 shows an optional technique for forming the stent/liner arrangement by molding.

A technique is indicated in FIG. 15 in which the collagen 12 is cast inside the stent 10 in a manner similar to that described in connection with FIG. 8. Upon set-up, the stent with a liner of cast collagen is removed from the mold and a hole may be formed through the collagen to provide a longitudinal opening therethrough. Otherwise, a mandrel or mold insert (not shown) may be used for this purpose also. Holes may also be formed through the stent walls in the collagen if the stent is perforated or the like.

The liner may be attached to the stent by any of several design features which may be incorporated into the stent. By providing the stent with hooks, or other similar topography (not shown), the sleeve may be readily attached to the stent. The sleeve material may be impaled on such barbs, thus securing the sleeve. With hooks of the appropriate size, the collagen material may not be perforated, but rather embedded in the holding topography.

As can be seen from the foregoing, the invention provides in one embodiment a stent in which collagen liner material is placed within and/or on the outside of the stent thereby reducing thrombus formation and therapeutically treating the vessel when a suitable agent is included in the collagen.

It is to be understood that the collagen material referred to herein as layers may be in the form of sheets associated with the stent or deposited thereon, i.e., as a coating.

Figures 16, 17, 18, 19, 20:
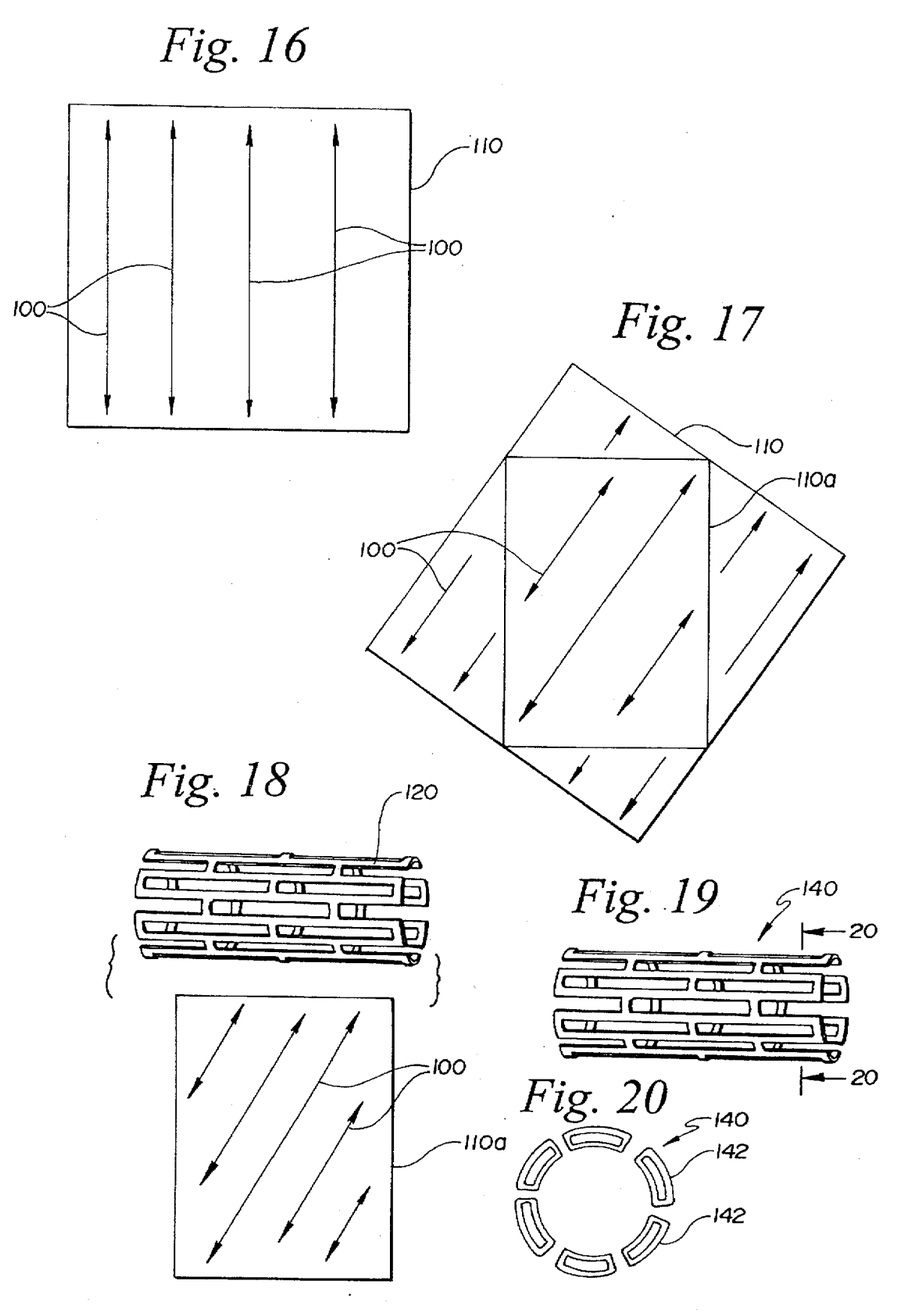
FIGS. 16, 17, and 18, schematically show the stretch of a collagen stent being oriented on a bias with respect to a stent.
FIGS. 19 and 20 show a coated stent, FIG. 20 being a cross-sectional view of FIG. 19.

Thus, the collagen material may be coated onto the stent surfaces as desired by spraying or dip coating or electrodeposition or the like or attached in other ways as described above. Such a coating might be about 1–50 microns thick. A coated stent is shown in FIG. 19, which will preferably be perforate as shown.

A collagen coated stent may also have a collagen sleeve over the collagen coating or under the collagen coating. For example, one may place a stent into a collagen sleeve, as shown in FIG. 1, with an interference fit. The inside of the stent may then be coated with collagen so that the stent and interior of the sleeve are covered and bonded together. Preferably, in such an arrangement, the sleeve will be SIS and the coating Type I or Type IV. It is also possible in the case of an open-work stent such as shown in FIG. 1 or 3, to coat the stent struts with collagen, place a collagen sleeve either over or inside the stem, or both, and then heat bond the sleeve and/or liner to the coating. This would preferably be done with Type IV collagen, especially SIS or with fibrin.

In some applications it may be desirable to include perforations in the collagen for fluid movement through the stent\collagen wall. Such an arrangement is readily obtained as stents are generally open or perforate with respect to their structure and perforations may be readily formed in a collagen liner, the perforations extending through the stent openings. Perforation in collagen liners of about 10–60 microns in diameter have been found satisfactory. The distribution of the perforations may be such as to be evenly spaced, such as at 30–60 micron spacing and to occupy about one-half of the liner surface areas. This, of course, may vary.

Lastly, there is a preferred orientation for placing collagen on the stent when the collagen is used in the form of a sheet which is wrapped around the stent or a tube inserted in the stent. It has been discovered that sheet collagen has the ability to stretch but that its stretchability is predominantly unidirectional. That is, most of the stretch is exhibited in one primary direction in a sheet. This is shown schematically by the parallel arrows 100 in FIG. 16 for a sheet of collagen 110 which typically shows little or no stretch in a direction normal to the arrows.

It has been discovered that the collagen sheet, when used as a sleeve or liner on a stent which undergoes expansion and/or contraction, can be better accommodated if the collagen sheet is associated with the stent on a "bias". This will be more fully explained by reference to FIGS. 17 and 18. If a piece of collagen sheet 110a is taken from sheet 110 in the orientations shown in FIG. 17, it can be seen that the stretch direction indicated by the arrows 100 is on a bias with respect to sheet 110a. In this case, the bias is 45° relative to the edges of sheet 110a. If sheet 110a is oriented normally with respect to a stent 120 as shown in FIG. 18, i.e., the edges of sheet 110a are normal to the longitudinal dimension of stent 120, when sheet 110a is wrapped around stent 120 to form a sleeve or rolled up (in direction shown at 112 in FIG. 18) into a tube for insertion into stent 120 as a liner, the stretch properties of sheet 110a will be on a bias with respect to the longitudinal dimension of stent 120, in this case the bias is 45°, which is a preferred bias. Other degrees of bias are acceptable but 45° is preferred.

It can be seen from the foregoing that due to the variable dimensions in both diameter and length which occurs with stents, such an arrangement better accommodates collagen sleeves and liners to dimensional changes in both directions without disruption at seams and without tears in the material.

One preferred type of stent for use in this invention is one of the type disclosed in related application 08/246,320, filed May 19, 1994, the entire content of which is incorporated herein by reference.

FIGS. 19 and 20 show a coated stent generally indicated at 140, the collagen coating 142 being best seen in FIG. 20. Coating 142 is shown on both the inside and outside surfaces of the stent although it may be on either as well.

It can be seen from the above that the invention also provides a treatment method of implanting a stent in which collagen material is placed between the stent and the vessel wall thereby reducing thrombus formation and therapeutically treating the vessel when a suitable agent is included in the collagen.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. In combination, a vascular prostheses comprised of an expandable support framework, the expandable support framework comprising a stent, which has an expanded state having a first diameter and a compressed state having a second diameter, the second diameter being smaller the first diameter, and is capable of being positioned at a targeted position within a lumen transluminally when the stent is in its compressed state, and a covering sleeve of a collagen material, the support framework and the covering sleeve being substantially the same length and substantially overlapping, and wherein the sleeve of collagen material is in sheet form and is oriented with respect to the longitudinal dimension of the stent such that the stretch properties of the collagen are on a bias with respect thereto.

2. The combination of claim 1 wherein the collagen material covers the stent inside and out.

3. The combination of claim 2 wherein the collagen is in the form of an outer sleeve and an inner sleeve.

4. The combination of claim 1 wherein the collagen material is comprised of collagen per se.

5. The combination of claim 1 wherein the collagen material is comprised of collagen on a support.

6. The combination of claim 5 wherein the support is a fabric.

7. The combination of claim 1 wherein the framework is a stent of variable diameter.

8. The combination of claim 7 wherein the stent is of the self-expanding type.

9. The combination of claim 1 wherein the sleeve has elastic properties.

10. The combination of claim 1 wherein the sleeve is sized large with respect to the framework at least before implantation.

11. The combination of claim 1 wherein the collagen includes added agent.

12. The combination of claim 11 wherein the agent is heparin.

13. The combination of claim 1 including a multi-layer arrangement of Type I and Type IV collagen material on the outside of the stent.

14. The combination of claim 13 wherein the Type IV is the outermost layer.

15. The combination of claim 14 wherein the Type IV is SIS.

16. In combination, a vascular expandable stent and a layer of collagen material in the form of a sleeve overlying the stent, the layer of collagen material being substantially the same length and substantially overlapping the stent so that when the combination is inserted within a vascular lumen, the layer of collagen material is positioned between the stent and the vascular wall of the lumen, and wherein the sleeve of collagen material is in sheet form and is oriented with respect to the longitudinal dimension of the stent such that the stretch properties of the collagen are on a bias with respect thereto.

17. In combination, a vascular prostheses comprised of a generally cylindrical expandable support stent, which has an expanded state having a first diameter and a compressed state having a second diameter, the second diameter being smaller than the first diameter, and is capable of being positioned at a targeted position within a lumen transluminally when the stent is in its compressed state, and an inner luminal liner comprising collagen material, wherein the collagen liner is in sheet form and is oriented with respect to the longitudinal dimension of the stent such that the stretch properties of the collagen are on a bias with respect thereto.

18. The combination of claim 17 wherein the collagen material comprises a bilayer arrangement.

19. The combination of claim 18 wherein one of the layers in the bilayer is a polymeric material.

20. The combination of claim 19 wherein the bilayer liner is comprised at least two types of collagen material.

21. The combination of claim 20 wherein the collagen material includes Type I and Type IV layers.

22. The combination of claim 21 wherein the Type IV is SIS.

23. The combination of claim 22 wherein the Type IV is the innermost layer and the Type I layer includes a drug.

24. The combination of claim 17 wherein the stent is of variable diameter.

25. The combination of claim 24 wherein the stent is of the self-expanding type.

26. The combination of claim 17 wherein the liner has cuffs at either end which overlap the ends of the stent.

27. The combination of claim 17 wherein the collagen includes an added agent.

28. The combination of claim 27 wherein the agent is heparin.

29. The combination of claim 17 wherein the stent has wall openings and the liner is perforated.

30. The combination of claim 29 wherein the perforations are about 10–60 microns in diameter.

31. The combination of claim 17 including SIS collagen material on the outside of the stent.

32. In combination, a vascular prosthesis comprised of an expandable stent, which has an expanded state having a first diameter and a compressed state having a second diameter, the second diameter being smaller than the first diameter, and is capable of being positioned at a targeted position within a lumen transluminally when the stent is in its compressed state, and inner and outer layer of SIS collagen material positioned on the stent, wherein at least one of the layers of collagen is in sheet form and is oriented with respect to the longitudinal dimension of the stent such that the stretch properties of the collagen are on a bias with respect thereto.

33. In combination, a vascular prosthesis comprised of an expandable stent, which is expandable from a first cylindrical position to a second cylindrical position and is capable of being positioned at a targeted position within a lumen transluminally when the stent is in its compressed state, a collagen coating on the stent and a collagen sleeve on the outside of the stent, wherein the sleeve of collagen is in sheet form and is oriented with respect to the longitudinal dimension of the stent such that the stretch properties of the collagen are on a bias with respect thereto.

34. The combination of claim 33 wherein the sleeve is SIS and the coating is Type I or Type IV.

35. An expandable stent, which is expandable from a first cylindrical position to a second cylindrical position and is capable of being positioned at a targeted position within a lumen transluminally when the stent is in its compressed state, comprised of a generally cylindrical body coated with a collagen material and carrying an overlying sleeve of collagen material, wherein the sleeve of collagen material is in sheet form and is oriented with respect to the longitudinal dimension of the stent such that the stretch properties of the collagen are on a bias with respect thereto.

36. The stent of claim 35 wherein the collagen coating is selected from the group consisting of Type IV and Type I.

37. The stent of claim 36 wherein the collagen sleeve is comprised of Type IV.

* * * * *

UNITED STATES PATENT AND TRADEMARK OFFICE
CERTIFICATE OF CORRECTION

PATENT NO. : 5,693,085
DATED : December 2, 1997
INVENTOR(S) : Andrew W. Buirge et al.

It is certified that error appears in the above-identified patent and that said Letters Patent is hereby corrected as shown below:

Title page,
Item [75], Inventors, after "all in Minn." add:
-- and Stephen F. Badylak, West Lafayette, Indiana. --

Signed and Sealed this

Twenty-second Day of February, 2005

JON W. DUDAS
*Director of the United States Patent and Trademark Office*